United States Patent
Wong et al.

(10) Patent No.: US 6,773,721 B1
(45) Date of Patent: **\*Aug. 10, 2004**

(54) OSMOTIC CAPLET

(75) Inventors: Patrick S.-L. Wong, Palo Alto, CA (US); Felix Theeuwes, Los Altos Hills, CA (US); George V. Guittard, Cupertino, CA (US); Atul D. Ayer, Palo Alto, CA (US)

(73) Assignee: ALZA Corporation, Mountain View, CA (US)

( * ) Notice: Subject to any disclaimer, the term of this patent is extended or adjusted under 35 U.S.C. 154(b) by 1826 days.

This patent is subject to a terminal disclaimer.

(21) Appl. No.: 08/442,210

(22) Filed: May 16, 1995

Related U.S. Application Data

(62) Division of application No. 07/970,519, filed on Nov. 2, 1992.

(51) Int. Cl.[7] .............................. A61K 9/24; A61K 9/26
(52) U.S. Cl. ........................................ 424/473; 424/469
(58) Field of Search .................................. 424/451, 473, 424/469–70, 456

(56) References Cited

U.S. PATENT DOCUMENTS

| | | | |
|---|---|---|---|
| 3,845,770 A | 11/1974 | Theeuwes et al. | 128/260 |
| 3,916,899 A | 11/1975 | Theeuwes et al. | 128/260 |
| 4,111,202 A | 9/1978 | Theeuwes | 128/260 |
| 4,111,203 A | 9/1978 | Theeuwes | 128/260 |
| 4,203,439 A | 5/1980 | Theeuwes | 128/260 |
| 4,327,725 A | 5/1982 | Cortese et al. | 128/260 |
| 4,612,008 A | 9/1986 | Wong et al. | 604/892 |
| 4,612,186 A * | 9/1986 | Eckenhoff et al. | 424/15 |
| 4,627,850 A | 12/1986 | Deters et al. | 604/892 |

OTHER PUBLICATIONS

Webster's New World Dictionary, 3rd Ed., 1988, p. 208, 209.*

* cited by examiner

*Primary Examiner*—Edward J. Webman
(74) *Attorney, Agent, or Firm*—Robert R. Neller

(57) ABSTRACT

An osmotic caplet is disclosed comprising an osmotic caplet exit for delivering a preselected dose of drug to a patient in need of therapy.

15 Claims, 1 Drawing Sheet

OSMOTIC CAPLET

This application is a division of application Ser. No. 07/970,519, filed Nov. 2, 1992, and benefit of the filing date of said earlier filed application is claimed under 35 U.S.C. § 120.

This invention pertains to an osmotic caplet. More particularly, this invention relates to an improvement in an osmotic caplet. The osmotic caplet comprises an improvement in the drug flow dynamics of the caplet governed by the ratio of delivery at least one delivery orifice or a plurality of orifices area $A_1$ to the caplet's internal cross-section area $\pi r^2$, to provide a means for delivering substantially one-hundred percent of the drug from the osmotic caplet. The invention concerns also a method for increasing the bioavailability of a drug by providing an osmotic caplet that delivers substantially one-hundred percent of a drug from the osmotic caplet, and substantially eliminate the start-up time of the delivery.

BACKGROUND OF THE INVENTION

Osmotic dosage forms for delivering a drug to a fluid environment of use are known to the drug dispensing art. For example, U.S. Pat. No. 3,845,770 issued to Theeuwes and Higuchi, and in U.S. Pat. No. 3,916,899, issued to the same patentees, Theeuwes and Higuchi, an osmotic dosage form is disclosed comprising a semipermeable wall that surrounds a compartment comprising a drug. The wall is permeable to the passage of fluid and there is a passageway through the wall for delivering the drug from the dosage form. The dosage forms of these patents, release the drug by fluid being imbibed through the wall into the compartment at a rate determined by the permeability of the wall and the osmotic pressure gradient across the wall to produce a solution of drug that is dispensed through the passageway from the dosage form. These dosage forms are extraordinarily effective for delivering a drug that exhibits an osmotic pressure gradient across the wall against the fluid. The dosage forms are effective also for delivering a drug mixed with an osmotically effective solute that is soluble in the fluid and exhibits an osmotic pressure gradient across the wall against an aqueous fluid.

A quantum improvement in osmotic dosage forms was presented to the medical and pharmaceutical dispensing art by inventor Theeuwes in U.S. Pat. Nos. 4,111,202; 4,111,203; and 4,203,439. In these patents, the delivery kinetics of the dosage form were enhanced for delivering a drug with varying degrees of solubility in an aqueous fluid. The kinetics are improved by manufacturing the dosage form with a drug compartment and an osmotic compartment separated by a film. These dosage forms deliver the drug by fluid being imbibed through the wall into the osmotic compartment producing a solution that causes the film to move and act as a driving force. The driving force pushes the drug through a small passageway from the dosage form.

A pioneer advancement in osmotic dosage forms was made by co-inventors Cortese and Theeuwes in U.S. Pat. No. 4,327,725 and by co-is inventors Wong, Barclay, Deters and Theeuwes in U.S. Pat. No. 4,612,008. The osmotic dosage form in these patents comprise a semipermeable wall that surrounds a compartment. The compartment contains a drug formulation and an expandable hydrogel. In operation, fluid is imbibed into the compartment where it contacts the drug formulation; thereby forming a dispensable formulation that is pushed by the expanding hydrogel from the dosage form.

A further and unexpected contribution to the drug dispensing art was provided by co-inventors Deters, Theeuwes, Mullins and Eckenhoff in U.S. Pat. No. 4,627,850. In this patent, the inventors provided an osmotic capsule comprising a wall capsulating and containing a drug formulation. The drug formulation is delivered through a very small orifice manufactured without any expressed ratio to the dimensions of the osmotic capsule. The osmotic capsule of this patent delivers an effective dose of drug over time.

The osmotic dosage forms described in the above patents operate successfully for their intended use and they deliver many difficult to deliver drugs for their intended therapeutic effects. Now, it has been observed, while these dosage forms are very effective and provide many advantages for delivering drugs for their intended therapy, there are a short comings associated with these dosage forms. In one manufacture, for example, these prior art dosage forms often embrace a conventional tablet shape that inherently retains or entraps drug in the inner top surface or within inner corners of the dosage form. In another manufacture, for example, the prior art dosage form embraces a conventional capsule shape comprising an inner configuration that entraps drug or restricts the flow of drug from the capsule in the immediate interior region adjacent to the orifice of the capsule; and in another instance, the drug is not delivered immediately and was delayed for hours before delivery of the drug.

It will be appreciated by those versed in the art in the light of the above presentation, that if an osmotic dosage form is provided that is essentially-free of the short comings known to the prior art, such an osmotic dosage form that would have a positive practical valve and it would also represent an advancement in the drug delivery art. The present invention advances the state of the drug delivery art by providing a novel and unique dosage form manufactured as an osmotic caplet for optimizing therapy by delivering essentially the full dose of drug present in the osmotic caplet. The osmotic caplet administers the drug at a programmed and controlled rate per unit time over a prolonged period of time. The osmotic caplet provides continuous over the administration of the drug, and the osmotic caplet maintains this control over an extended period of time.

OBJECT OF THE INVENTION

Accordingly, it is an immediate object of this invention to provide a dosage form manufactured as an osmotic caplet for delivering a drug, and which osmotic caplet overcomes the limitations associated with the prior art.

Another object of the invention is to provide an osmotic caplet that can house a dose of drug and deliver essentially all of the drug for providing the intended therapy of the drug.

Another object of the invention is to make available an improvement in an osmotic caplet, wherein the improvement comprises means for maximizing the amount of drug delivered from the osmotic caplet by providing an internal convex surface that surrounds the orifice of the delivery system.

Another object of the invention is to make available an osmotic caplet characterized by an improvement in flow dynamics governed by a ratio of orifice diameter $D_1$ to an internal caplet diameter $D_2$ for increasing the dose of drug delivered thereby substantially eliminating drug entrapment within the caplet.

Another object of the invention is to make available an osmotic caplet comprising means for enhancing the hydrodynamic drug delivery properties of the caplet by providing a caplet with a physical structure free of corners thereby eliminating residual drug retained in the corners of the caplet at the termination of a drug delivery period.

Another object of the invention is to make available a caplet that is tasteless, easily administered, easier to swallow than tablets, is solid and oblong-shaped with a curved lead end for enhancing the delivery of the medicament comprising the caplet.

Another object of this invention is to make available a solid-oblong osmotic tablet designed as an osmotic caplet with enhanced drug bioavailability for oral administration to a patient in need of drug therapy.

Another object of this invention is to provide an osmotic caplet for delivering in vivo a drug that is difficult to deliver and now can be delivered by the osmotic caplet of this invention in a therapeutically effective dose per unit time over time.

Another object of this invention is to provide an osmotic caplet for administering a drug to the gastrointestinal tract by making available an osmotic caplet comprising at least one wall that maintains its integrity in the gastrointestinal tract during the osmotic caplet transit through the gastrointestinal tract.

Another object of the invention is to provide an osmotic caplet comprising a wall capleting a solid drug formulation that optionally includes a pharmaceutically acceptable carrier, which drug is delivered by the osmotic caplet at meaningful and useful therapeutic rates over a prolonged period of time.

Another object of the invention is to make available an osmotic caplet comprising at least one or a plurality of osmotic caplet orifices of any shape provided the number of caplet orifices individually or totally added together is a certain fraction of the internal cross-section of the cylindrical osmotic caplet.

Another object of this invention is to provide an osmotic caplet systems in which drug will be delivered immediately after ingestion without the delay of start-up time characteristic of the prior art osmotic system including osmotic push-pull systems.

Another object of this invention is to provide an osmotic caplet comprising an inner wall comprising of a water-swellable composition that swells at a controlled rate and encaplets a drug formulation, and an outer wall comprising a semipermeable composition that maintains its physical and chemical integrity and encaplets the inner wall.

Another object of the invention is to provide an osmotic caplet comprising a compartment containing a drug, which compartment is surrounded by a caplet wall comprising an osmotic-caplet orifice for delivering a drug from the caplet over a prolonged period of time of at least 15 minutes to thirty hours.

Another object of the invention is to provide an osmotic caplet comprising high drug loading of a drug, makeup once-a-day dosing of a up to 1200 mg in soluble drug in a single swallowable tablet.

Another object of the invention is to provide an osmotic caplet comprising a large osmotic caplet orifice for delivering insoluble drug formulations from the osmotic caplet.

Another object of the invention is to provide an osmotic caplet comprising an exterior instant drug-containing coat that releases the drug immediately in vivo for immediate therapy.

Another object of the invention is to provide an osmotic caplet comprising at least one large orifice or a plurality of orifices equivalent to a large orifice for delivering an aqueous or biologically fluid insoluble drug from the osmotic caplet.

Another object of the invention is to provide an osmotic caplet comprising a cylindrical-shape semipermeable body comprising a curved lead end with an accompanying orifice both designed for minimizing drug retention inside the osmotic caplet and a rear end.

Other objects, features and advantages of the invention will be more apparent to those skilled in the art from the following specification, taken in conjunction with the accompanying drawings and claims.

BRIEF DESCRIPTION OF THE DRAWINGS

In the drawing figures, which are not drawn to scale, but are set forth to illustrate various manufacturers of the invention, the drawing figures are as follows.

Drawing

Drawing

Drawing

Drawing

Figure 1:
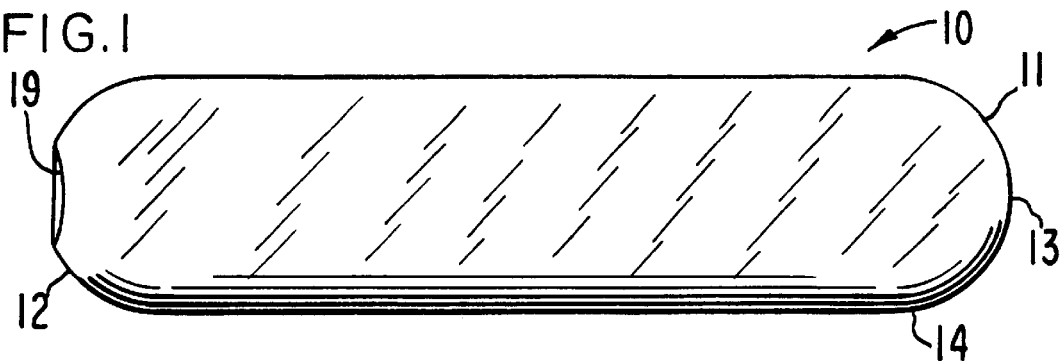
FIG. 1 illustrates one manufacture of an osmotic caplet comprising a continuous body with a pair of curved-rounded ends for both increasing the dose of drug delivered and for increasing the swallowability of the osmotic caplet.

DETAILED DESCRIPTION OF THE DRAWING FIGURES.

Turning now to the drawing figures in detail, which drawing figures are examples of an osmotic caplet provided by the invention, and which examples are not to be construed as limiting, one example of an osmotic capsule is seen in drawing FIG. 1. In drawing FIG. 1, an osmotic caplet 10 is seen comprising a body 11 and a lead end 12 and a trailing or rear end 13. Osmotic caplet 10 comprises a wall 14 that surrounds an internal compartment, not seen in drawing FIG. 1.

Figure 2:
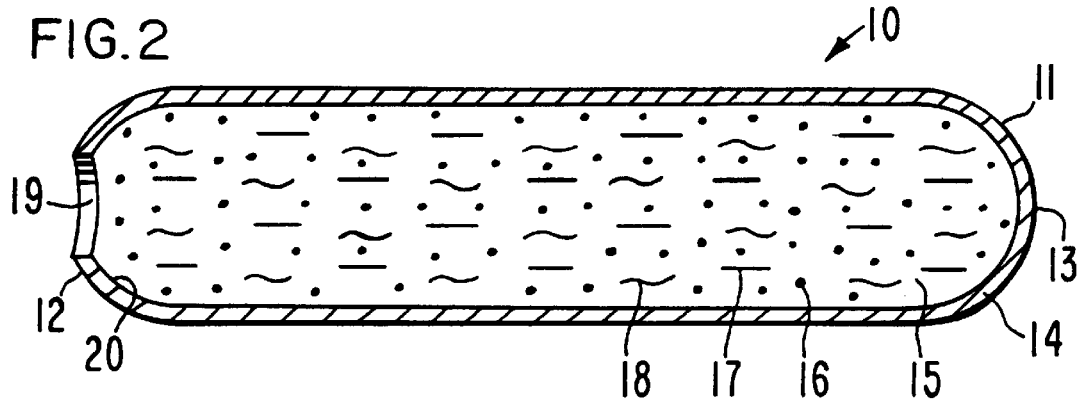
FIG. 2 illustrates a longitudinal view of an osmotic caplet comprising an oblong-body terminating in rounded ends of reduced diameter relative to the internal diameter of the oblong-body of the osmotic caplet, with the osmotic-caplet comprising a semipermeable wall.

Drawing FIG. 2 depicts the osmotic caplet 10 of drawing FIG. 1 in opened section in drawing FIG. 2. The osmotic caplet 10 is illustrated as an oblong-shaped initially solid medicament invented for delivering the maximum dose of a drug. In a presently preferred manufacture, osmotic caplet 10 is made comprising a single unit body 11 comprising a lead end 12 and a rear end 13.

Osmotic caplet 10 comprises a wall 14 that surrounds an internal compartment 15. Wall 14 is semipermeable, that is, wall 14 is permeable to the passage of a fluid, aqueous or biological fluids, present in an environment of use, such as an animal or human. Semipermeable wall 14 is nontoxic, substantially inert, and wall 14 maintains its physical and chemical integrity during the drug dispensing life of caplet 10. The phrase, keeps its physical and chemical integrity, means wall 14 does not lose its physical and chemical integrity during the dispensing life of osmotic caplet 10.

Compartment 15 comprises an effective amount of drug 16 10 represented by dots. Drug 16 in one embodiment, is soluble to very soluble in an external fluid imbibed through semipermeable wall 14 into compartment 15, and drug 16 exhibits an osmotic pressure gradient across wall 14. Drug 16, in another embodiment exhibits a limited solubility in fluid imbibed into compartment 15, and it exhibits a limited osmotic pressure gradient across wall 14. In this latter embodiment, drug 16 optionally mixed with an osmagent 17, presented as dashes, which osmagent 17 is soluble in the external fluid and it exhibits an osmotic pressure gradient across wall 14 for aiding in dispensing drug 16 from osmotic caplet 10. Drug 16 can be present in compartment 15 with an optional member selected from the group consisting of a binder, dispersant, wetting agent, suspending agent, lubricant and dye, represented by wavy line 18. Representative of the members including suspending agents such as colloidal magnesium, silicon dioxide, and calcium silicate; binders like polyvinyl pyrrolidone, lubricants like magnesium stearate, and wetting agents such as fatty amines and fatty quaternary ammonium salts. A dye can be present in the compartment 15 for aiding in identifying a drug 16 present in caplet 10.

Osmotic dosage caplet 10 comprises a dispensing passageway 19 that communicates the interior of compartment 15 with the exterior of solid dosage caplet 10. Dispensing passageway 19 is present in wall 14 in the area where wall 14 is curved upward and outward from inside compartment 15 for directing the maximum movement or flow of drug 16 from compartment 15. The curved, inside surface 20 and its continual rate of curved change eliminates sharp breaks, angularity, or corners thereby substantially eliminating drug 16 entrapment at the inside surface 20 of caplet 10. The caplet drug delivery end 12 improves the flow profile resulting in a minimum to none amount of residual drug 16 in caplet 10.

Passageway 19 is a wide-passageway characterized by a geometry distinctive from the conventional passageways of the prior art dosage forms. In the passageway 19, provided by this invention, the convex surface 20 on the inside drug side of wall 12 possesses a radius of curvature $r_w$, where $r_w$ is equal to or larger than the radius of osmotic caplet 10 designed as a cylinder with a cylindrical radius, r, but not exceeding 2r. The convex surface on the drug side 20 can be, in one embodiment, a cone shape. The height of the cone is at least equal or greater than the radius of the cylindrical portion of the caplet, r, and the preferred 2×r. In the preferred manufacture, passageway 19 is positioned at the tip of the convex surface of the drug surface 20 of wall 12. The passageway area optionally can be as large as the cylindrical cross-section area of the caplet, wherein the diameter is D. In the presently preferred dosage caplet 10, the area of the passageway $A_1$ where $A_1=0.1$ to $0.9$ is for a cylinder having a cylindrical cross-section area of $\pi r^2$. The dimensions of the osmotic caplet are presently expressed in millimeters. Caplet passageway 19, in another manufacture comprises a multiplicity of orifices in the convex surface 20, with the total area of the multiplicity of caplet passageways 19 less than the cross-sectional area of the oblong osmotic caplet 10 at its widest area.

Dosage caplet 10 possessing the present passageway 19 exhibits performance characteristics exemplified by an absence of start-up time for the osmotic caplet 10 for delivering drug 16; dosage caplet 10 possesses the ability to deliver small doses and large doses of soluble and insoluble drugs from 300 nanograms to 1200 milligrams dose of drug over a 24 hour drug delivery period; dosage caplet 10 comprises internal compartment for containing excipients helpful for delivering a peptide or protein, often protective agents and flux enhancers are co-delivered with the drug; and, dosage caplet 10 can deliver microparticles in which the small pellets are delivered to lessen mucosal irritation.

Figure 3:
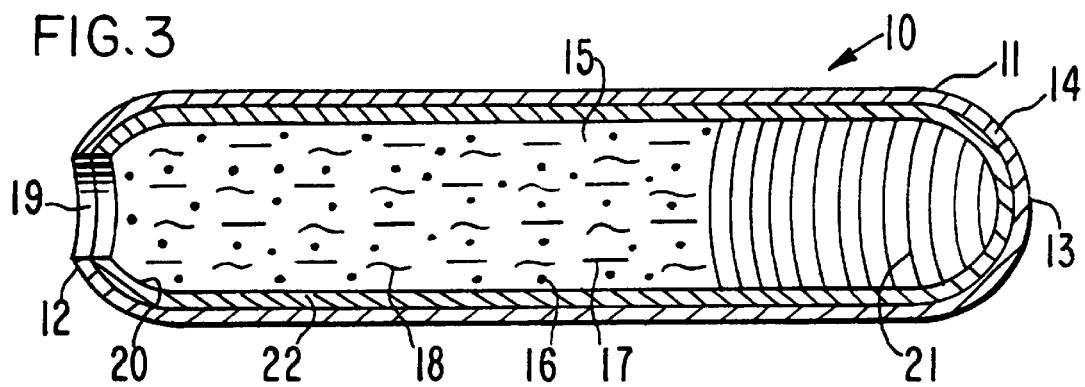
FIG. 3 illustrates another manufacture of an osmotic caplet provided by the invention comprising an outer semipermeable wall and an inner gelatin wall with the caplet comprising at least one of a member selected from the group consisting of an osmagent and an osmopolymer.

Drawing FIG. 3 depicts, in opened section, the osmotic caplet 10 of drawing FIG. 1. The osmotic caplet 10, of drawing FIG. 3, comprises a body 11 comprising lead end 12, rear end 13, wall 14 and compartment 15. Compartment 15 comprises drug 16 and an osmopolymer 21, or an expandable driving member, identified by curve lines. Osmopolymer 21 is in contact with the drug 16 composition. The drug 16 composition layer and the osmopolymer 21 layer operate in union for delivering the maximum dose of drug 16 through opened passageway 19. Compartment 15 optionally comprises a member 18 selected from the group consisting of a binder, dispersant, wetting agent, suspending agent, lubricant, and dye. Osmotic caplet 10 comprises additionally an internal wall 22 that faces compartment 15 and is in layered arrangement with the internal surface of wall 14. Internal wall 22 is non-toxic and it does not adversely affect drug 16 and other members 18 present in compartment 15. Internal wall 22 is permeable to the passageway of aqueous and biological fluids, and it comprises a hydrophilic polymeric composition that swells in the presence of fluid imbibed into compartment 15.

Figure 4:
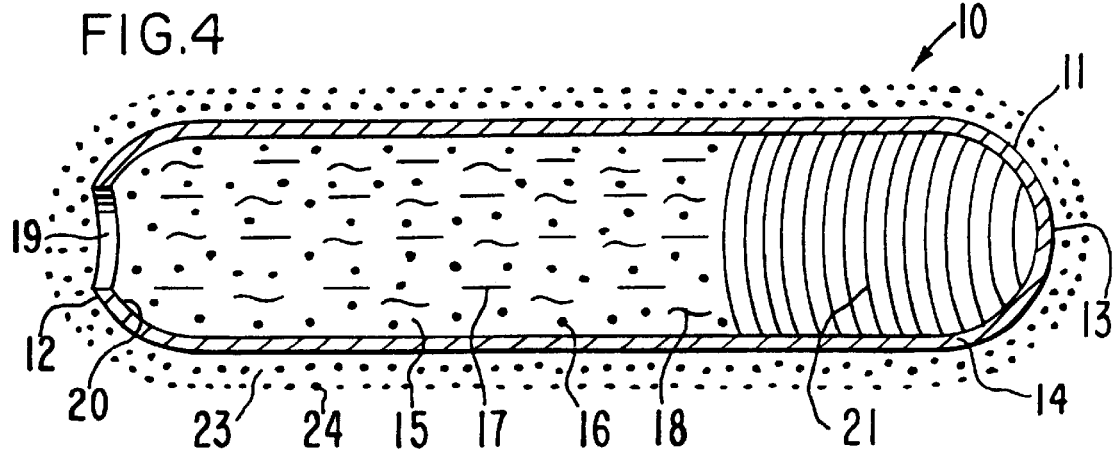
FIG. 4 illustrates another manufacture of an osmotic caplet provided by the invention comprising a dosage of drug in an instant-release coat on the exterior of the caplet for immediate release for instant therapy; and, In the drawings and in the specification, like parts in related figures are identified by like numbers. The terms that appear earlier in the specification and in the description of the drawing figures, as well as in embodiments thereof, are further detailed elsewhere in the disclosure.

Drawing FIG. 4 depicts, in opened section, the osmotic caplet 10. Osmotic caplet 10 comprises a body 11 comprising lead 12, trailing-end 13, outside wall 14 and compartment 15. Compartment 15 comprises drug 16, an osmagent 17, an osmopolymer 21, and a member 18 selected from the group consisting of a binder, dispersant, wetting agent, suspending agent, lubricant and dye. Osmotic caplet 10, in drawing FIG. 4, additionally comprises a coat 23 on the exterior surface of semipermeable wall 14. Coat 23 comprises an aqueous or biological composition and it contains drug 24. Coat 23 comprising drug 24 provides drug 24 for making available drug 24 instantly. In operation, when osmotic caplet 10, is in a fluid environment, coat 23 dissolves or undergoes dissolution and concurrently delivers drug 24 to a biological drug receptor. Coat 23 comprising drug 24 by providing immediate drug 24 delivery, thereby overcomes any time that may be needed before drug 16 is delivered from compartment 15 through passageway 19. Coat 23, upon hydration in an aqueous environment, operates independently of compartment 15, which compartment 15 delivers drug 16 by imbibing fluid through wall 14 and then hydro-osmotically delivering drug 16 from osmotic caplet 10.

DETAILED DESCRIPTION OF THE INVENTION

Drawing FIGS. 1 through 4 are illustrative of osmotic caplet 10 that can be manufactured according to the invention. In accordance with the practice of this invention, osmotic caplet 10 is manufactured with a semipermeable wall 14 that does not adversely affect drug 16, the components comprising osmotic caplet 10, and an animal, including a human patient host. Semipermeable wall 14 is permeable to the passage of external fluid such as water and biological fluids, and it is substantially impermeable to the passage of drug 16. The selectively semipermeable wall compositions are non-erodible, nontoxic, and they are insoluble in fluids. Typical materials for forming wall 14 in one embodiment are cellulose esters, cellulose ethers and cellulose ester-ethers. These cellulosic polymers have a degree of substitution, D.S., on the anhydroglucose unit from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and acetyl content up to 21%; cellulose acetate having an acetyl content of 32 to 39.8%: cellulose diacetate having a D.S. of 1 of 2 and an acetyl content of 21 to 35%; cellulose triacetate having a D.S. of 2 to 3 and an acetyl content of to 44.8%; and the like. More specific cellulosic polymers include cellulose propionate having a D.S. of 1.8 and a propionyl content of 39.2 to 45% and a hydroxyl content of 2.8 to 5.4%; cellulose acetate-butyrate having a D.S. of 1.8, and acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like.

Additional semipermeable polymers for wall 12 include acetal-dehyde dimethyl acetate, cellulose acetate ethyl carbamate, cellulose acetate phthalate for use in environments having a low pH, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the co-precipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride), semipermeable polymers exhibiting a fluid permeability of $10^{-5}$ to $10^{-1}$ (cc.mil/cm$^2$.hr.atm) expressed as per atmosphere of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, J. R. and Roff W. J., 1971, published by CRC Press, Cleveland, Ohio.

Inner wall 22, in contact with external wall 14 comprises in a presently preferred manufacturer gelatin. The gelatin used for the present purpose comprises a viscosity of 10 to 40 millipoises and a bloom strength up to 150 grams; and gelatin comprising a bloom value of 160 to 250. The inner wall 22 can comprises 100 weight percent gelatin, or in another manufacturer inner wall 22 can comprises 60 wt % to 99 wt % gelatin, and 1 wt % to 40 wt % of a polysaccharide selected from the group consisting of agar, acacia, karaya, tragacanth, algin and guar.

Coat 23 comprising drug 24 is coated onto the exterior surface of semipermeable wall 14. Coat 23 comprises an aqueous soluble carrier that provides instant drug 24 to a patient in from zero time to seventy-five minutes. Coat 23 comprises at least one member selected from the group consisting of hydroxyalkylcellulose, such a hydroxypropylmethylcellulose, hydroxybutylmethylcellulose, hydroxyethylmethylcellulose, and sodium carboxymethylcellulose. Coat 23 carrier additionally embraces a member selected from the group consisting of polyvinylpyrrolidone, polyvinylalcohol, polyvinylpyrimidine, gelatin, polysaccharide, a blend of polyvinylpyrrolidone and gelatin, polyethylene oxide, and a blend of polyvinylpyrrolidone and an alkylcellulose, such as methylcellulose. The dose of drug 24 in coat 23 is 150 nanograms to 350 milligrams.

The expressing drug 16 in compartment 15 includes a drug that produces a physiologically or pharmacologically effect in animals including humans. The term physiologically denotes the administration of a drug to produce normal functions in a patient and the term pharmacologically denotes variations in response to the dose of drug administered to an animal. The terms are defined in Stedman's Medical Dictionary, 1966, published by Williams & Wilkins, Baltimore, Md. The term drug as used herein means the drug is in the compartment by itself, or the drug is in the compartment mixed with an osmotic solute, binder, dye, mixtures thereof, and the like. The drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synoptic sites, neuroeffector junctional sites, endocrine and hormone systems, immunological system, reproductive system, skeletal system, inhibitory of autocoids and histamine systems. The active drug that can be delivered for acting on these animal systems includes depressants, hypnotics, sedatives, psychic energizers, tranquilizers, anticonvulsants, muscle relaxants, antiparkinson agents, analgesics, anti-inflammatory, local anesthetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents and cardiovascular drugs.

Drugs 16 that act on the central nervous system include hypnotics and sedatives, including pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and a-bromoisovaleryl urea; hypnotic and sedative urethanes and disulfanes; psychic energizers such as isocoboxazid, nialamide, phenelzine, imipramine, tranylcypromine and parglyene; tranquilizers such as chloropromazine, promazine, fluphenazine, reserpine, deserpidine, meprobamate, and benezodiazepines such as chlordiazepoxide; anticonvulsants such as primidone, enitabas, diphenylhydantoin, ethotoin, phenetu-ride and ethosuximide; muscle relaxants and antiparkinson agents such as mephenesin, methocarbomal, trihexlphenidyl, and biperiden; anti-hypertensives such as methyldopa and L-β-3-4-dihydroxyphenylalanine, and pivaloyloxyethyl ester of α-methyldopa hydrochloride dihydrate; analgesics such as morphine, codeine, meperidine, nalorphine, antipyretics and anti-inflammatory agents such as aspirin, indomethacin, salicylamide, naproxen, colchicine fenoprofen, sulidac, diclofenac, indoprofen and sodium salicylamide, local anesthetics such as procaine, lidocaine, maepaine, piperocaine, tetracaine and dibucane; antispasmodics and muscle contractants such as atropine, scopolamine, methscopolamine, oxyphenonium, papaverine; prostaglandins such as $PGE_1$ $PGE_2$, $PGE_{18}$, $PGE_{28}$ and PGA; anti-microbials such as penicillin, tetracycline, oxytetracycline, chlorotetracycline, chloramphenicol and sulfonamides; anti-malarials such as 4-aminoquinolines, 8-aminoquinolines and pyrimethamine; hormonal agents such as prednisolone, cortisone, cortisol and triamcinolone, androgenic steroids such as methyltesterone, and fluoxmesterone; estrogenic steroids such as 17β-estradiol, α-estradiol, estriol, α-estradiol 3-benzoate, and 17-ethynyl estradiol-3-methyl ether; progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β10α-pregna-4,6-diene-3,20-dione; sympathomimetic drugs such as epinephrine, amphetamine, ephedrine and norepinephrine; hypotensive drugs such as hydralazine, cardiovascular drugs such as procainamide, procainamide hydrochloride, amyl nitrite, nitroglycerin, dipyridamole, sodium nitrate and mannitol nitrate; diuretics such as chlorothiazide, acetazolamide, methazolamide and flumethiazide; antiparasitics such as bephenium, hydroxynaphthoate, dichlorophen and dapsone; and neoplastics such as nechlorethamine, uracil mustard, 5-fluorouracil, 6-6-thioguanine and procarbazine; a lipid regulating agent including gemfibrozil β-blockers such as pindolol, propranolol, practolol, metoprolol, oxprenolol, timolol, atenolol, alprenolol, and acebutolol; hypoglycemic drugs such as insulin, isophane insulin, protamine zinc insulin suspension, globin zinc insulin, extended insulin zinc suspension, tolbutamide, acetohexamide, tolazamide and chlorpropamide; antiulcer drugs such as cimetidine; nutritional agents such as ascorbic acid, niacin, nicotinamide, folic acid, choline, biotin, pantothenic acid, and vitamin $B_{12}$; essential amino acids; essential fats; eye drugs such as pilocarpine, pilocarpine salts such as pilocarpine nitrate, pilocarpine hydrochloride, dichlorphenamide, atropine, atropine sulfate, scopolamine and eserine salicylate; histamine receptor antagonists such as cimetidine; and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumarate and sodium lactate; and drugs that act on α-adrenergic receptors such as clonidine hydrochloride. Drug 16, in another manufacture, is an antiviral drug for treating viral injections comprising a member selected from the group consisting of didanosine, zidovardine, zalcitabine, acyclovir, fluxuridine, ribavirin, cytarabine, vidarabine, azidouridine, ganciclovir, deoxynojirmycin, fiacitabine, fialuridine, fluorothymidine, dideoxycitidine, nevirapine, staviudine, dideoxyinosine, isoprinosine, and foscarnet. The beneficial drugs 16 are known to the art in Remington's Pharmaceutical Sciences, 14th Ed., 1970, published by Mack Publishing Co., Easton, Pa.; and in The *Pharmacological Basis of Therapeutics*, by Goodman and Gilman, 4th Ed., 1970, published by the MacMillan Company, London, and in U.S. Pat. No. 4,576,604.

Drug 16 can be in various therapeutic forms, such as uncharged molecules, molecular complexes, pharmacologically acceptable salts such as inorganic, organic, hydrochloride, hydrobromide, sulfate, laurylate, palmitate, phosphate, nitrite, oleate and salicylate. For acid drugs 24, salts of metals, amines, or organic cations, quaternary ammonium derivatives can be used for the presence purpose. Derivatives of drug 16, such as an ester, ether and amide can be used for the present purpose. A drug that is water insoluble can be used in a form that is a water soluble derivative thereof to effectively serve as a solute, and on its administration form osmotic caplet 10, it is converted by enzymes, hydrolyzed by the body pH or other metabolic processes to the original drug form, or to a biologically active form. Drug 24 in coat 23 can be the same as drug 16 in compartment 15, or drug 24 in coat 23 can be a different drug 24 than drug 16 in compartment 15. Generally, compartment 15 comprises 300 nanograms, ng, to 1200 milligrams, mg, of drug 16 for administered at 5 ng to 850 mg over a prolonged period up to 24 hours, hrs. In another embodiment, individual osmotic caplet 10 can be provided comprising 1 mg, 5 mg, 50 mg, 100 mg, 125 mg, 200 mg, 275 mg, 500 mg and 650 mg. The osmotic caplet 10 can be administered once, twice or thrice daily.

The osmagent 17 that can be used for the purpose of this invention comprise inorganic and organic, preferably a solid compound that exhibits an osmotic pressure gradient across an external fluid across semipermeable wall 14. The osmagents are known also as osmotically effective compounds, osmotic solutes, and osmotic fluid imbibing agents. The osmagents are used by mixing the osmagent with drug 16 that has a limited solubility in the external fluid to provide an osmotic solid composition, that after fluid is imbibed into caplet, an osmotic drug solution that is hydrodynamically and osmotically delivered from osmotic caplet 10. The phrase limited solubility as used herein means the drug has a solubility of less than 1% by weight in an aqueous fluid present in the environment. The osmagents are used by homogenously or heterogenously mixing the osmagent with the drug and then changing the blend into a caplet or pressing the blend into a shape corresponding to the shape of osmotic caplet 10, which is then surrounded with semipermeable wall 14. The osmagent attracts fluid into caplet 10 producing a solution which is delivered from the caplet concomitantly transporting undissolved and dissolved drug to the exterior of caplet 10. Osmagent 17 used for the purpose of this invention comprises a member selected from the group consisting of a salt, oxide, carbohydrate, acid, ester, magnesium sulfate, magnesium chloride, sodium chloride, potassium chloride, lithium chloride, potassium sulfate, sodium sulfate, lithium sulfate, lithium phosphate, sodium phosphate, potassium phosphate, potassium acid phosphate, calcium lactate, mannitol, urea, inositol, magnesium succinate, tartaric acid, carbohydrates such as raffinose, sucrose, glucose, lactose monohydrate, and a blend of fructose glucose.

The osmagent is initially present in excess and it can be any physical form such as particle, crystal, pellet, tablet, strip, film or granule. The osmotic pressure of saturated solutions of various osmotically effective compounds and for mixtures of compounds at 37° C., in water, is listed in Table 1. In the table, the osmotic pressure π, is in atmospheres, ATM. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 1, osmotic pressures of from 20 ATM to 500 ATM are set forth; of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by Hewlett Packard Co., Avondale, Pa.

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |

-continued

| COMPOUND OR MIXTURE | OSMOTIC PRESSURE ATM |
|---|---|
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Dextrose | 82 |
| Potassium Sulfate | 39 |
| Mannitol | 38 |
| Sodium Phosphate Tribasic.12H$_2$O | 36 |
| Sodium Phosphate Dibasic.7H$_2$O | 31 |
| Sodium Phosphate Dibasic.12H$_2$O | 31 |
| Sodium Phosphate Dibasic Anhydrous | 29 |
| Sodium Phosphate Monobasic.H$_2$O | 28 |

The osmopolymer 17, operable for pushing drug 17 composition from caplet 10 comprises a hydrophilic polymer. Hydrophilic polymers are known also as osmopolymers. The osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 60 fold volume increase. The osmopolymers can be noncross-linked or cross-linked. The swellable, hydrophilic polymers are, in one presently preferred embodiment, lightly cross-linked, such as cross-links being formed by covalent or ionic bonds. The osmopolymers can be of plant, animal or synthetic origin. Hydrophilic polymers suitable for the present purpose include poly(hydroxyalkylmethacrylate) having a molecular weight of from 30,000 to 5,000,000; poly (vinylpyrrolidone) having molecular weight of from 10,000 to 360,000; anionic and cationic hydrogels; polyelectrolyte complexes, poly(vinyl alcohol) having a low acetate residual, cross-linked with flyoxal, formaldehyde, or glutaraldehyde and having a degree of polymerization from 200 to 30,000; a mixture of methyl cellulose, cross-linked agar and carboxymethyl cellulose; a water insoluble, water swellable copolymer reduced by forming a dispersion of finely divided copolymer of maleic anhydride with styrene, ethylene, propylene, butylene or isobutylene cross-linked with from 0.00001 to about 0.5 moles of polyunsaturated cross-linking agent per mole of maleic anhydride in the copolymer; water swellable polymers of N-vinyl lactams, and the like.

Other osmopolymers include hydrogel polymers such as Carbopol® acidic carboxy polymers generally having a molecular weight of 450,000 to 4,000,000; the sodium salt of Carbopol® acidic carboxy polymers and other metal salts; Cyanamer® polyacrylamides; cross-linked water swellable indenemaleic anhydride polymers; Goodrite® polyacrylic acid having, but not limited to, a molecular weight of 80,000 to 200,000, and the sodium and other metal salts; Polyox® polyethylene oxide polymers having a molecular weight of 100,000 to 7,500,000; starch graft copolymers; Aqua-Keeps® acrylate polymers; diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels, in U.S. Pat. No. 4,576,604 issued to Guittard et al.; in U.S. Pat. No. 4,855,141 issued to Eckenhoff et al.; and in *Handbook of Common Polymers*, by Scott and Roff, published by the Chemical Rubber, CRC Press, Cleveland, Ohio.

The solubility of a drug in the fluid can be determined by known techniques. One method consists of preparing a saturated solution comprising the fluid plus the drug as ascertained by analyzing the amount of agent present in a definite quantity of the fluid. A simple apparatus for this purpose consists of a test tube of medium size fastened upright in a water bath maintained at constant temperature and pressure, in which the fluid and the drug are placed and stirred by a rotating glass spiral. After a given period of stirring, a weight of the fluid is analyzed and the stirring continued an additional period of time. If the analysis shows no increase of dissolved drug after successive periods of stirring, in the presence of excess solid drug in the fluid, the solution is saturated and the results are taken as the solubility of the product in the fluid. If the drug is soluble, an added osmotically effective compound optionally may not be needed; if the drug has limited solubility in the fluid, then an osmotically effective compound can be incorporated into the device. Numerous other methods are available for the determination of the solubility of a drug in a fluid. Typical methods used for the measurement of solubility are chemical and electrical conductivity. Details of various methods for determining solubilities are described in *United States Public Health Service Bulletin*, No. 67 of the Hygienic Laboratory; *Encyclopedia of Science and Technology*, Vol. 12, pp 542 to 556, 1971, published by McGraw-Hill, Inc.; and *Encyclopedia Dictionary of Physics*, Vol. 6, pp 547 to 557, 1962, published by Pergamon Press, Inc.

The present invention manufactures an osmotic caplet 10 by surrounding a pressed solid caplet-shaped solid body 11 with a semipermeable wall 14, or first with a gelatin wall 22 followed by a semipermeable wall 14. One method of manufacture comprises inserting a pressed body into a caplet channel machine leaving one end exposed that is dipped into a wall-forming bath to coat the exposed end, followed by dipping the other uncoated end into the bath to surround the end with a wall-forming composition. In one manufacture, the caplet is coated with a semipermeable wall and then permitted to dry with rotation for spreading evenly the wall-forming semipermeable wall around the body of the caplet. In another manufacture, a gelatinous coating is applied to the first end and then to the second end of the body of the caplet. Next, after the caplet is permitted to dry and then followed by coating the body of the caplet in a semipermeable wall-forming bath. Inner wall 22 can in another manufacture comprise a coating consisting of a water soluble polymer such as a hydroxyethylcellulose, hydroxypropylmethylcellulose and hydroxypropylcellulose. Inner wall 22 in this manufacture serves as a lubricating wall 22 to facilitate high drug loading of osmotic caplet 10 and to facilitate the uninhibitated delivery of drug 16 from osmotic caplet 10. That is, lubricating wall 20 substantially eliminates resistance of drug 16 delivery from osmotic caplet 10.

Another manufacture comprises filling a caplet die with the composition to be compressed into a shape corresponding to the die cavity, and then removing the compressed body from the cavity. The die cavity is lubricated prior to filling the cavity to present sticking and to make it easy to remove the compressed caplet-shaped body from the die cavity. The die cavity may be lubricated with a lubricant such as stearic acid, magnesium stearate, calcium stearate, sodium lauryl sulfate or potassium lauryl sulfate. Next, the caplet body is surrounded with a wall. A wall can be applied by using standard wall-coating equipment. Equipment that can be used for coating the compressed body include the Accela-Cote® coater, High-Cota® or the Wurster® suspension coater. The coaters often comprise a vaporizer to facilitate drying, and an exhaust system designed to remove any possible dust. The coating can be effected by using spray guns, and atomizing equipment to introduce a wall-forming solution into a coating pan, or to introduce a wall-forming solution into an air suspension column. Optionally, cold or warm air can be introduced into the spraying cycle to regulate coating and/or drying of the coated caplet. The coating solution can be applied by using a peristaltic spray pump or a pneumatic displacement pump, in continuous or interrupted spray and dry patterns. The coating composition is sprayed to a preselected desired thickness, usually for each separate wall 0.25 mm to 10 mm.

Another manufacture that can be used for coating a pressed caplet body, previously pressed in a plate process, rotary die process, a reciprocating die process, or a continuous rotary press, or high pressure station rotary press, or high pressure station rotary press, in one manufacture comprises placing a caplet-forming film over a lower mold with the caplet forming formulation poured onto the film. Then, a film of a wall-forming composition is placed over the caplet body followed by the top mold. The mold set is placed under a press and pressure applied with or without heat to form the caplet. The caplet can be made with a passageway. The passageway is integrally formed by the mold set equipped with a passageway-forming area that presents coating in the passageway area.

Another manufacture of caplet 10, is manufactured by standard granulation techniques. For example, the caplet forming ingredients are formulated by the wet granulation technique using an organic cosolvent, such as isopropyl alcohol-methylene dichloride, 80/20, v/v, (volume/volume) as the granulating fluid. The ingredients forming the caplet comprising the drug and other caplet forming ingredients are individually passed through a 40 mesh screen and then thoroughly blended in a blender. Next, a polymer, for example, poly(vinylpyrrolidone) is dissolved in a portion of granulation fluid, in the cosolvent described above. Then, the poly(vinylpyrrolidone) solution is slowly added to the dry powder blend with continual mixing in a blender. The granulation fluid is added until a wet blend is produced, generally about 400 cc of granulating fluid per kilogram of blend. The wet mass blend then is forced through a 20 mesh screen onto trays and dried for 18 to 30 hours at 40° C. to 60° C. The dried granules are sized with a mesh screen. Next, a lubricant such is magnesium stearate is added to the dry screened granular blend, and the blend passed through an 80 mesh screen.

In another process the drug and other caplet-forming compositions are blended in a fluid bed granulation. After the powders are dry blended, a granulation fluid comprising an aqueous granulation fluid is sprayed onto the powders an dried in a granulation. This process granulates all of the ingredients together while adding the granulation solution. After the granules are dried, a lubricant such as magnesium stearate is added to the granulation.

The caplet forming blend, in either of the above processes, is then pressed into a caplet using a tablet press. The speed of the press is set optionally at 30 rpm and the maximum load set at 0.5 to 20 tons. Then, the caplet body is surrounded with a wall.

The osmotic caplet, in another manufacture is made by mixing a drug with an osmagent and/or an osmopolymer, and pressed into a solid possessing dimensions that corresponds to the internal dimensions of the caplet; or the drug and other caplet formulation forming ingredients and a solvent are mixed by conventional methods such as ballmilling, calendering, stirring or rollmilling, and then pressed into a preselected shape. Next, a layer of a composition comprising an osmagent, and/or an osmopolymer is placed in contract with a layer of drug formulation, and then the two contacting layers, except for a caplet mouth, are surrounded with a semipermeable wall. The wall can be applied by protecting the caplet mouth to keep it open free from coating with a semipermeable wall forming material. The wall can be applied by molding, spraying, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds and coats the two pressed compositions. The air suspension procedure is described in U.S. Pat. No. 2,799,241; J. Am. Pharm. Assoc. Vol. 48, pp 451–59 (1979); and, ibid, Vol. 49, pp 82 to 84 (1960). Other standard manufacturing procedures are described in Modern Plastics Encyclopedia, Vol. 46, pp 62 to 70 (1969); and in Pharmaceutical Science, by Remington, 14th Ed., pp 1626 to 1978 (1970), published my Mack Publishing Co., Easton, Pa.

Exemplary solvents suitable for manufacturing include inert inorganic and organic solvents that do not adversely harm the materials and the final. The solvents broadly include members selected from the group consisting of aqueous solvents, alcohols, ketones, esters, ethers, aliphatic hydrocarbons, halogenated solvents, cycloaliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, etrachloroethane, ethyl ether, isopropyl ether, cyclohexane, cyclooctane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DESCRIPTION OF EXAMPLES

The following examples are illustrative of the present invention, and they should not be considered as limiting the scope of the invention in any way, as these examples and other equivalents thereof will become apparent to those versed in the art in the light of the present disclosure, the drawings and the accompanying claims.

Example 1

An osmotic oblong-shaped solid caplet is manufactured with a wide, passageway as follows: first, 300 mg of ranitidine hydrochloride, a histamine $H_2$ receptor antagonist for inhibiting both daytime and nocturnal basal gastric acid secretion, including gastric acid secretion stimulation is blended with 11.0 mg of hydroxypropylmethylcellulose having a 11,200 molecular weight, 27 mg of microcrystalline cellulose having a 0.09 mm particle size and a 36,000 molecular weight, 36 mg of polyvinylpyrrolidone having a 35,000 molecular weight, and 5 mg of magnesium stearate, are dry blended for 17 to 20 minutes in a blender to produce a homogenous blend. Next, the dry blend is wetted with 350 mL of anhydrous ethanol, followed by drying the blend in an oven for 20 hours at 30° C. Next, the dried granules are passed through a 20 mesh screen, and compressed under 2.5 tons in an oblong-shaped dye to yield a solid caplet-shaped composition.

Next, the pressed composition is inserted into a caplet-retaining member that covers the caplet in the passageway-forming area and simultaneously permits the body of the caplet exposed for receiving a wall-forming composition.

Next, the exposed caplet body is surrounded with a permeable wall-forming composition by dipping the exposed surface into the composition. The wall-forming composition comprises 55 wt % cellulose acetate comprising an acetyl content of 39.8%, 43 wt % polyvinylpyrrolidone having a 42,000 molecular weight, and 2 wt % tripropyl citrate are dissolved in a cosolvent comprising methylene chloride-methanol, 85 wt %–15 wt %, to obtain 5% solids. The wall-forming composition is coated around the opposed caplet by drying until a uniform wall is applied, to about 5.5 mg per wall.

Finally, the osmotic caplet is removed from the caplet-holding member, and dried in a forced air oven at 50° C. for 50 hours to evaporate the solvents. The osmotic caplet comprises an orifice opening of 0.1 of the area of the cylindrical cross-section of the caplet.

Example 2

The procedure of Example 1 is repeated in this example with all the manufacturing steps as previously set forth, except that in this example the permeable wall is coated on its exterior surface with an instant release ranitidine salt coat. The instant coat is applied to the exterior semipermeable wall from a composition comprising 60 mg of ranitidine hydrochloride, 120 mg of mannitol, and 120 mg of hydroxypropylmethylcellulose having a 11,200 molecular weight in distilled water, and dried to yield an instant release coat. The osmotic caplet provides instant release ranitidine therapy from the exterior coat followed by ranitidine therapy from inside the osmotic caplet.

Example 3

An osmotic caplet is provided to produce an oral, osmotic caplet providing the procedures of Examples 1 and 2, wherein the osmotic caplet comprises 20 mg of famotidine, a competitive inhibitor of histamine $H_2$ on the exterior surface and 125 mg of famotidine inside the osmotic caplet.

Example 4

An osmotic caplet for dispensing cimetidine to a patient in need of cimetidine therapy is prepared as follows: first, 35 kg of cimetidine hydrochloride is passed through a sizing screen and then added to the bowl of a fluid bed granulator. Next, 1.46 kg of polyvinylpyrrolidone having a 360,000 molecular weight is mixed with distilled water and the fluid prepared is fed into the granulator in small volumes to dampen the cimetidine hydrochloride. The resulting granulation is dried and passed through a standard 20 mesh screen. Next, 0.178 kg of magnesium stearate is added to the granules and blended with the granules. The granules are fed to a caplet dye and pressed under 2.5 tons of pressure into a caplet-shaped solid dosage form. The caplet comprises cimetidine hydrochloride 87.3 wt %, 6.3 wt % polyvinylpyrrolidone, 0.5 wt % magnesium stearate, and 5.9 wt % bound water.

Next, the caplet-shaped solid dosage is inserted into a hollow, caplet housing member that both holds the caplet and covers its lead end to provide a caplet passageway formed during coating the remainder of the caplet with semipermeable wall. The semipermeable composition comprises 50 wt % cellulose acetate comprising 39.8% acetyl content is homogeneously blended with 40 wt % polyvinylpyrrolidone comprising a 42,000 molecular weight, and 8 wt % hydroxypropylmethylcellulose is mixed with an acetone-methyl alcohol cosolvent 80 wt %–20 wt %, comprising 6% solids, and mixing continued until a clear solution resets. Next, the compressed caplets in the housing member are placed in a coater, and the caplets coated on the exposed areas with the wall-forming composition. A wall comprising 39.7 mg of cellulose acetate, 30.7 mg of polyvinylpyrrolidone, 6.5 mg of hydroxypropylmethylcellulose and 1.5 mg of tripropyl citrate is coated to each exposed caplet. The wall composition weighed 78.4 mg. The coated caplets are removed from the coater a convex lead end with a 1 mm passageway, and a cross-section of 8 mm. The osmotic caplet delivery the cimetidine in the upper gastrointestinal tract.

Example 5

The procedure of Example 4 is followed in this example, except in this example, the osmotic caplet comprises a dose amount of a drug selected from the group consisting of omeprazole, nizatidine, bifentidine, erbrotidine, nifentidine, roxatidine and lansoprazole.

Example 6

An osmotic caplet comprising 50 mg of carbidopa, an inhibitor of aromatic amino acid decarboxylation, and 200 mg of levodopa the metabolic precursor of dopamine that crosses the blood-brain barrier and is converted, to dopamine for the treatment of Parkinson's disease is prepared by blending the carbidopa and levodopa with 150 mg of poly(ethylene oxide) having a 200,000 molecular weight, 30 mg of hydroxypropylmethylcellulose stearate, and 18 mg of microcrystalline cellulose having a 36,000 molecular weight, are blended into a homogenous mass and passed through a 40 mesh screen. Next, 1 mg of mannitol is passed through a mesh screen and all the screened ingredients are added to the bowl of a laboratory blender and the ingredients dry blended for 20 minutes to produce a homogenous blend. Then, a granulation fluid is prepared comprising 250 mL of ethanol and 250 mL of isopropyl alcohol by stirring the solvents, and the granulation fluid added to the bowl of the blinder. Then, 20 mL of the granulating fluid is sprayed into the bowl with constant blending, then 35 mL of the granulation fluid is added and the mess blended for 15 to 20 minutes. Then, the wet granules are passed through a 16 mesh screen and dried at room temperature for 24 hours.

Next, a second osmotic push composition is prepared by blending 55 mg of poly(ethylene oxide) having a 5,000,000 molecular weight, mg of sodium chloride and 1.5 mg of magnesium stearate are passed through a 40 mesh screen, and the ingredients added to a mixing bowl, and all the ingredients blended for 10 to 15 minutes. Then, a granulation fluid is prepared by mixing 75 mL of methanol and 150 mL of isopropyl alcohol, and the granulation fluid slowly added to the bowl and the wet blend mixed for 15 to 20 minutes to produce a homogenous blend. Next, the wet blend is passed through a 16 mesh screen, spread on a stainless steel tray and dried at room temperature of 22.5° C. for 24 hours.

A number of solid caplet cores are prepared by pressing the two compositions comprising the drug composition and the expandable, push composition in a caplet cavity mold and compressing the two layers into an oblong shape. Next, the caplet cores lead end one placed into a caplet mold and the exposed surface coated with a permeable polymeric composition comprising cellulose acetate having a 39.8% acetyl content, poly(ethylene glycol) 4,000, methylene chloride and methanol. The caplets are coated in their uncoated area until this area is coated with a wall. A Wurster® air suspension coated caplets are removed from the caplet mold and then spread on a tray. The solvent is evaporated in a circulating air oven at 50° C. for 60 hours. The osmotic caplet is administered orally to a patient in need of treating Parkinson's disease.

Example 7

The procedures of the above examples are followed in this example, to provide an osmotic caplet comprising a convex curved lead end defining a caplet passageway, and wherein the osmotic caplet comprises a member selected from the group consisting of biperiden hydrochloride, biperiden lactate, trihexyphenidyl hydrochloride, diphenhydramine hydrochloride, benztropine mesylate, procyclidine hydrochloride, selegiline addition salt, selegiline hydrochloride, selegiline palmate, hyoscyamine sulfate, and hyoscyamine hydrobromide.

Example 8

An osmotic caplet comprising a convex wall formed by the wall bulged outward at the lead end and comprising an exit port in the convex wall is prepared as follows: first, 160 mg of tandospirone, and 120 mg of poly(ethylene oxide having a 200,000 molecular weight are added to a Freund Flo-Coater's® bowl, a fluid bed granulator, and the drug and the polymer mixed in an air suspension for 5 minutes to produce a homogenous blend. Next, a solution prepared by dissolving 100 g of poly(vinylpyrrolidone) having a 27,500 molecular weight and 1,566 g of water are sprayed onto the homogenous blend. Next, the coated blend was dried, and the granules removed from the granulator. Next, the granules are mixed with 2.25 mg of calcium stearate and 0.25 mg of butylated hydroxytoluene, to produce caplet granules.

Next, a push composition is prepared by blending 130 mg of poly(ethylene oxide) comprising a 7,500,000 molecular weight, 35 mg of osmagent sodium chloride, and 0.6 mg of ferric oxide are separately screened through a 40 mesh screen and then blended into a homogenous blend. Next, 30 mg of hydroxypropylmethylcellulose having a 11,200 molecular weight is blended with the screened, homogenous blend to produce a resultant blend. This latter lend is mixed with 30 mg of denatured, anhydrous alcohol, for 5 minutes, passed through a 20 mesh screen, allowed to dry at 22° C. for 10 hours, and again passed through a 20 mesh screen. The screened push composition is blended with 0.25 mg of magnesium stearate, and screened to produce the granules.

Next, the tandospirone drug composition and the push osmopolymer-osmagent composition are compressed in contacting bilayered arrangement in a caplet dye. The compositions are compressed in the length or vertical direction of the caplet to provide a convex, curved bulged outward lead end and a curved trailing end. The two contacting compositions are compressed under a pressure of two tons.

Next, the caplet body is inserted into a caplet holder that covers the lead end and permits the remainder of the caplet body to be exposed for receiving a gelatin coat. The gelatin coat comprises gelatin, erythrosin, iron oxide and titanium dioxide in an aqueous carrier. The exposed surfaces are coated with a thin 0.1 mm coat. Other gelatin coats, from 0.1 mm to 7.5 mm can be coated onto the caplet surface. The gelatin coat is overcoated with a laminated semipermeable wall composition comprising cellulose acetate having an acetyl content of 32% using an air suspension coater. The semipermeable wall forming composition comprises 5% polymer in acetone-water, 90:10, wt/wt, is used to form the semipermeable wall 0.07 mm thick. The osmotic caplet is removed from the caplet holder, and dried to evaporate the solvents.

Example 9

The above examples are followed in this example for manufacturing an osmotic caplet comprising a lead end possessing a semipermeable bulged wall having a wide passageway with the caplet comprising 25 mg to 750 mg of a drug selected from the group consisting of quinapril, indolapril, olindapril, rentiapril, spirapril, cilazaprilat, lisinopril, imidapril, benazeprilat, cilazapril, alacepril, captopril, delapril, fosinopril, libenzapril, pentopril, perindopril, altiopril, quinaprilat, ramipril, spiraprilat, teprotide, zofenopril, enalapril, benazepril, enalaprilat, antipain, and cilastatin.

Example 10

An elongated dosage form is manufactured as an osmotic caplet comprising a length of 22 mm and a diameter of 8.5 mm at its center, and a curved lead end comprising a caplet passageway is manufactured according to the processes of this invention, with the caplet comprising 15 mg to 750 mg of a drug selected from the group consisting of amrinone, bepridil, diltiazem, felodipine, fendiline, flunarizine, nicardipine, isradipine, nifedipine, nimodipine, nisoldipine, nitredipine, perhexiline, amlodipine, nilvadipine, prenylamine, verapamil, cinnarizine, gallopamil, belfosdil, and fostedil.

Example 11

The manufacturing procedure in the above examples are followed to provide an osmotic caplet comprising 500 ng to 1000 mg of antiviral drug selected from the group consisting of didanosine, zidovudine, zalcitabine, acyclovir, fluxuridine, ribavirin, cytarabine, vidarabine, azidouridine, ganciclovir, deoxynojirmycin, fiacitabine, fialuridine, fluorothymidine, foscarnet, dideoxycitidine, nevirapine, staviudine, dideoxyinosine, and, isoprinosine.

Example 12

An osmotic caplet is prepared as follows: first, a drug composition comprising 525 mg of the insoluble base drug nifedipine is blended with 140 mg of poly(ethylene oxide) having a 175,000 molecular weight, and 7.5 mg of sodium chloride to produce a uniform blend. Then 0.75 mg of calcium stearate is added to the blend, all the ingredients blended, and screened through a 40 mesh screen to produce uniform particles. Next, a caplet displacement composition is prepared comprising 70 mg of sodium carboxymethylcellulose, 10 mg of sodium chloride and 1 mg of magnesium stearate are blended for minutes in a stainless steel blender. Next, the blend is screened through a 40 mesh screen to yield caplet displacement particles. Then, the drug particles and the displacement particles are dried separately, and the two respective particle composition pressed into contacting layers under pressure of 3.25 tons.

The pressed layers are next inserted into a caplet mold and the exposed caplet body sprayed with a wall-forming composition comprising 80 wt % cellulose acetate having a 43.3% acetyl content, 7.5 wt % of hydroxypropylmethylcellulose comprising a 9,200 molecular weight, 10 wt % of poly(vinylpyrollidone) having a 39,000 molecular weight, and 2.5 wt % of tributyl citrate in a methylene chloride-ethanol to surround the exposed caplet body with a semipermeable wall. The wall is permeable to aqueous fluids and impermeable to drug. The osmotic caplet comprises a large osmotic caplet orifice to effect the delivery of essentially all of the drug. The osmotic caplet is free of the need for drug over loading because essentially all the drug is delivered from the osmotic caplet. In contrast, a noncaplet dosage form requires excess drug to deliver a given dose of drug to compensate for the drug retained in the noncaplet dosage form. Moreover, the osmotic caplet exhibits instant drug delivery from the caplet, and is essentially free of the delay known to the prior at delivery system.

Example 13

An embodiment of this invention pertains to the use of an easy-to-swallow osmotic caplet in a method for administering a drug to the gastrointestinal tract of a patient in need of drug therapy, wherein the use of the osmotic caplet comprises: (1) admitting the osmotic caplet orally into the patient in need of therapy, the osmotic caplet comprising: (a) an oblong body; (b) a dose amount of 10 mg to 750 mg of drug in the caplet; (c) a semipermeable wall defining the caplet; said caplet characterized by: (d) a convex lead end comprising a passageway as means for maximizing the delivery of drug from the caplet; (2) imbibing fluid through the semipermeable wall into the caplet; thereby (3) delivering the drug to the patient to provide the needed therapy over a prolonged period of time up to 24 hrs. The easily swallowed osmotic caplets and their solid content are essentially free from tampering and provide uniformity and precision of the dosage administered to the patient. Examples of drugs that can be administered include a member selected from the group consisting of acetaminophen, aspirin, acyclovir, gemfibrozil, ibuprofen, naproxen, methyldopa, carbidopa, levodopa, selegiline, zidovudine, didanosine, and dideoxycitidine. In summary, it will be appreciated the present invention contributes to the drug dispensing art by providing an unobvious and unique dosage form that possesses a practical utility, and can administer a drug at a metered release rate up to 24 hours for preselected therapy.

While the invention has been described and pointed out in detail with reference to operative embodiments thereof, it will be understood by those skilled in the art that various changes, modifications, substitutions and omissions can be made without departing from the spirit of the invention. It is intended, therefore, that the invention embraces those equivalents within the scope of the claims which follow.

We claim:

1. An osmotic caplet for delivering a maximum dose of a drug to a patient, the osmotic caplet comprising:
   (1) a cylinder body;
   (2) a dose of 300 ng to 1,200 mg of drug in the caplet;
   (3) a semipermeable wall that defines the caplet; and, wherein the osmotic caplet is characterized by:
   (4) a lead end comprising a convex surface with a passageway for substantially eliminating residual drug inside the caplet, which convex surface possesses a radius of curvature equal to but not exceeding twice the radius of the cylinder body, for maximizing the dose of drug delivered from the osmotic caplet.

2. The osmotic caplet for delivering the maximum dose of drug according to claim 1, whereas the cylinder comprises a length greater that its width.

3. The osmotic caplet for delivering, the maximum dose of drug according to claim 1, wherein the osmotic caplet is an osmotic solid caplet.

4. The osmotic caplet for delivering the maximum dose of drug according to claim 1, wherein the drug exhibits an osmotic pressure gradient across the permeable wall.

5. An osmotic caplet for delivering a maximum dose of a drug to a patient, the osmotic caplet comprising:
   (1) a cylinder body;
   (2) a dose of 300 ng to 1,200 mg of drug in the osmotic caplet;
   (3) an osmagent in the osmotic caplet;
   (4) a semipermeable wall that defines the caplet; and wherein the osmotic caplet is characterized by:
   (5) a convex end comprising a passageway with an inside surface possessing a radius of curvature r and not exceeding 2r of the cylinder body for delivering one-hundred percent of the drug from the osmotic caplet during the drug delivery period.

6. The osmotic caplet for delivering the maximum dose of drug according to claim 4, wherein the drug is a member selected from the group consisting of cimetidine, ranitidine, famotidine, nizatidine, bifentidine, erbrotidine, nifentidine, roxatidine, omeprazole, and lansprazole.

7. An osmotic caplet for delivering a maximum dose of drug to a patient, said osmotic caplet comprising:
   (1) a body longer in proportion to its width;
   (2) a dose of 300 ng to 1,200 mg of drug comprising a member selected from the group consisting of quinapril, indolapril, olindapril, rentiapril, spirapril, cilazaprilat, lisinopril, imidapril, benazeprilat, cilazapril, alacepril, captopril, delapril, fosinopril, libenzapril, pentopril, perindopril, altiopril, quinaprilat, ramipril, spiraprilat, teprotide, zofenopril, enalapril, benazepril, enalaprilat, antipain, and cilastatin;
   (3) a semipermeable wall that surrounds the body; and wherein the osmotic caplet is characterized by:
   (4) an end comprising a passageway for eliminating drug entrapment inside the caplet, said end comprising a convex surface with a radius of curvature r and not exceeding 2r of the caplet body width, thereby delivering the dose of drug from the osmotic caplet.

8. The osmotic caplet for delivering a maximum dose of drug to a patient, according to claim 6, wherein the drug in the osmotic caplet is replaced by a drug comprising a member selected from the group consisting of amrinone, bencyclone, bepridil, diltiazem, felodipine, fendiline, flunarizine, nicardipine, isradipine, nifedipine, nimodipine, nisoldipine, nitredipine, perhexiline, amlodipine, nilvadipine, prenylamine, verapamil, cinnarizine, fendiline, gallopamil, belfosdil, and fostedil.

9. An osmotic solid caplet for delivering a dose of drug to a patient, said osmotic caplet comprising:
   (1) a body possessing a length in millimeters greater than its width in millimeters;
   (2) a dose of 300 ng to 1,200 mg of drug in the osmotic caplet;
   (3) a gelatinous coat surrounding the body;
   (4) a semipermeable wall surrounding the gelatinous coat;
   (5) an end comprising an inside surface that eliminates residual drug retention in the osmotic caplet, said end comprising a radius of curvature r and not exceeding 2r of the width of the caplet body; and, (6) a passageway in the end for delivering the drug from the osmotic caplet over a prolonged period of time.

10. An osmotic caplet for delivering a dose of drug to a drug receiving environment, said osmotic caplet comprising:
    (1) a cylinder comprising a length greater than its width in millimeters;
    (2) a dose of drug in a first layer in the osmotic caplet;
    (3) a push composition in a second layer in the osmotic caplet;
    (4) a wall surrounding the body;
    (5) an end next to the first layer integral in the permeable wall; and
    (6) a passageway for delivering the drug by hydro-osmotic energy from the osmotic caplet over a prolonged period of time, and wherein the osmotic caplet is characterized by the absence of a start-up time required for drug delivery and the end possessing a radius of curvature not exceeding the radius of the body width for reducing residual drug in the caplet as the end of delivering the dose of drug.

11. The osmotic caplet for delivering a drug according to claim 9, wherein the drug is a member selected from the group consisting of acetaminophen, aspirin, ibuprofen, acyclovir, gemfibrozil, selegiline, methyldopa, carbidopa, and levodopa.

12. The osmotic caplet for delivering a drug according to claim 9, wherein a composition comprising a drug and an immediate release pharmaceutically acceptable carrier is in contact with the exterior of the semipermeable wall.

13. An osmotic caplet for delivering a drug to a patient, said osmotic caplet comprising:
    (a) a cylinder;
    (b) a dose of 300 ng to 1,200 mg of an antiviral drug in the oblong body;
    (c) a semipermeable wall permeable to the passage of fluid and impermeable to the passage of drug that surrounds the oblong body;
    (d) a convex end for delivering a one-hundred percent dose of antiviral drug, said convex end comprising a radius of curvature not exceeding twice the radius of the oblong body for obtaining the desired effect.

14. The osmotic caplet for delivering an antiviral drug according to claim 12, wherein the antiviral drug is a member selected from the group consisting of zidovudine, didanosine, acyclovir, and dideoxycitidine.

15. The osmotic caplet for delivering an antiviral drug according to claim 12, wherein the antiviral drug is a member selected from the group consisting of zalcitabine, fluxuridine, ribavirin, cytarabine, vidarabine, azidouridine, gancidovir, deoxynojirmycin, fiacitabine, fialuridine, fluorothymidine, foscarnet, nevirapine, staviudine, dideoxyinosine, and isoprinosine.

* * * * *